(12) United States Patent
Müller-Lierheim

(10) Patent No.: US 6,387,127 B1
(45) Date of Patent: May 14, 2002

(54) FOLDABLE INTRA-OCULAR LENS

(76) Inventor: Wolfgang Müller-Lierheim, Sambergerstrasse 8, D-81477 München (DE)

( * ) Notice: Subject to any disclaimer, the term of this patent is extended or adjusted under 35 U.S.C. 154(b) by 0 days.

(21) Appl. No.: 09/486,765

(22) PCT Filed: Sep. 1, 1998

(86) PCT No.: PCT/EP98/05540

§ 371 Date: May 12, 2000

§ 102(e) Date: May 12, 2000

(87) PCT Pub. No.: WO99/11303

PCT Pub. Date: Mar. 11, 1999

(30) Foreign Application Priority Data

Sep. 2, 1997 (DE) .......................................... 197 38 345

(51) Int. Cl.⁷ .................................................. A61F 2/16
(52) U.S. Cl. ........................................ 623/6.59; 264/1.7
(58) Field of Search ................................ 623/FOR 105, 623/6.11, 6.56, 6.59, 6.6; 264/1.7

(56) References Cited

U.S. PATENT DOCUMENTS

| 4,304,895 A | 12/1981 | Loshaek |
| 4,687,485 A | 8/1987 | Lim et al. |
| 4,731,079 A | 3/1988 | Stoy |
| 4,871,785 A | 10/1989 | Froix |
| 4,997,441 A | * 3/1991 | Sulc et al. .................... 623/6.6 |
| 4,997,442 A | 3/1991 | Barrett |
| 5,002,570 A | 3/1991 | Sulc et al. |
| 5,211,662 A | 5/1993 | Barrett et al. |
| 5,217,491 A | 6/1993 | Vanderbilt |

FOREIGN PATENT DOCUMENTS

| DE | 19623289 | 12/1997 |
| EP | 0492126 | 7/1992 |
| FR | 2609425 | 7/1988 |
| FR | 2757065 | 6/1998 |

* cited by examiner

Primary Examiner—David H. Willse
(74) Attorney, Agent, or Firm—Crowell & Moring LLP

(57) ABSTRACT

An intraocular lens includes (1) a foldable optical lens part made of a copolymer; and (2) a harder haptic part. A high crosslinking of the copolymer of the lens part and of the haptic part results in a high stability against hydrolysis in a biological medium.

8 Claims, No Drawings

FOLDABLE INTRA-OCULAR LENS

BACKGROUND AND SUMMARY OF INVENTION

The invention relates to an intraocular lens.

Such an intraocular lens is disclosed in U.S. Pat. No. 5,217,491. The known intraocular lens consists of a foldable optical lens part made of a soft, especially swellable material, as for example pHEMA (polyhydroxyethyl methacrylate) or a copolymer thereof, and a harder haptic part of PMMA (polymethyl methacrylate). In this disclosure it is furthermore stated that the experiment was undertaken to produce a lens blank in which the core forming the optical lens part is formed from a HEMA-MMA copolymer and a harder ring surrounding the latter for the later haptic of PMMA. In the case of a pHEMA/MMA ratio of 75:25, the core could be pressed out from a disc-shaped blank. With a pHEMA/MMA ratio of 50:50 the core was tight in the outer ring, but the core separated from the PMMA ring after hydration in water.

In a further test a lens blank was produced in which the core intended for the optical lens part was prepared from a HEMA-MMA copolymer with a HEMA/MMA ratio of 75:25 with a harder haptic ring of PMMA with small HEMA percentages in an MMA/HEMA ratio in the starting solution of 90:20 and 80:20. For the lens blank with a pHEMA/MMA ratio of 75:25, a tight bond was formed between the haptic ring and the optical core. The latter lens blank did not have, however, sufficiently lasting hydrolysis stability. This is also the case with the lens blank in which the core is made by the polymerization of HEMA and TEGDMA as crosslinker, the core is then swollen and then a PMMA ring is formed around the core using EGDMA as crosslinker.

EP 0 269 288 A1 discloses the use of a copolymer of 80 g HEMA and 20 g MMA as material for an intraocular lens. It is also known from this disclosure to add EDGMA to a copolymer in a ratio of admixture of 65:35.

DE 38 00 529 A1 has disclosed a copolymer of 85% HEMA and 15% MMA crosslinked with 0.5% EDGMA for the production of an intraocular lens. What is involved is copolymers of a low degree of crosslinkage.

U.S. Pat. No. 4,871,785 discloses primarily copolymers containing HEMA for the production of contact lenses, which are also said to be suitable for intraocular lenses, and in which a high percentage of crosslinking agent is used.

Particularly in the biological environment of the eye no long-term resistance to hydrolysis is obtained. This is due mainly to the fact that the aqueous humor and enzymes present therein have a hydrolyzing effect on the lens material, especially the optical part thereof.

The invention is addressed to the problem of creating an intraocular lens of the kind referred to above, which will have sufficient long-term stability under hydrolysis, especially in the biological environment of the eye.

DETAILED DESCRIPTION OF INVENTION

The invention is characterized in that the HEMA-ethyl methacrylate copolymer (lens material) and the HEMA-MMA- and HEMA-ethyl methacrylate copolymer (optical lens part) is formed from a greatly crosslinked matrix with three-dimensional network. On account of the great crosslinking and the content of MMA and ethyl methacrylate, the necessary hydrolysis stability of the copolymer forming the lens material and the optical lens part is achieved. Particularly in the biological environment of the eye, very good long-term stability and biocompatibility are achieved with the lens according to the invention. It is furthermore advantageous that the intraocular lens can be steam-sterilized in autoclaves at 121° C. The lens consists of a hydratable lens material and optical lens part in a hard haptic. In this consistency the lens can be folded for implantation, and the haptic can be made in a known manner sufficiently stiff to assure a precise positioning of the intraocular lens in the implanted state in the eye, especially in the posterior chamber.

The lens according to the invention can be made from a combination blank whose core is formed by the HEMA-MMA- or HEMA-ethyl methacrylate copolymer and which is surrounded by a hard ring of PMMA, PEMA (polyethyl methacrylate) or an MMA-ethyl methacrylate copolymer. The final haptic form can be made from the hard ring by mechanical working, for example grinding or the like.

To achieve the great crosslinkage, in a combination blank, a common crosslinking agent is used for the HEMA-MMA copolymer of the optical lens part, and the PMMA, PEMA or MMA-ethyl methacrylate copolymer of the haptic part. This crosslinker has at least two functional reactive groups which react with chains of the starting monomers entirely independently of one another. In this manner the chains are bound to form a three-dimensional network. Ethylene glycol dimethacrylate (EGDMA) is used as crosslinking agent. The content of HEMA in the copolymer of the lens material and optical lens part can be 80 to 95 wt.-%. The content of MMA and ethyl methacrylate in the copolymer is about 4 to 17 wt.-%. The crosslinking agent content in the copolymer amounts to about 0.5 to 2.0 wt.-%.

The production of the lens blank can be performed as follows. A perforated disk of PMMA or PEMA or an MMA-ethyl methacrylate copolymer is press-fitted into a polymerization mold, preferably made of polypropylene. This combination of the polymerization mold and the perforated disk is transferred to the polymerization apparatus. The solution to be polymerized, which contains HEMA, MMA or ethyl methacrylate, the crosslinker, especially EGDMA, and an UV absorber, is placed in the center bore of the disk, and then polymerized.

The polymerization is performed in a conventional manner and is based on radical polymerization. The UV absorber is especially 4-methacryloxy-2-hydroxybenzophenone (MAO-2-HBP) with the formula:

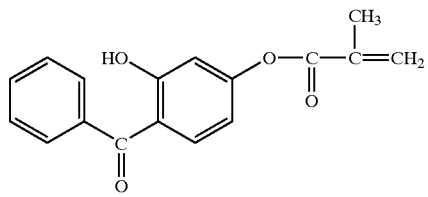

This UV absorber contains a reaction center (=CH$_2$) which permits its installation into the three-dimensional polymer matrix.

An appropriate starter, especially a chemical starter, for example α,α'-azoisobutyronitrile (AIBN), serves to initiate the polymerization. The starter substance is added in a proportion of about 0.1 wt.-%. The reaction is completely polymerized in the mold at elevated temperature, especially at 40° C., for about 48 hours. Then follows an annealing of the polymer at about 60° C. to 70° C. for about five hours. In some cases a post-treatment can be performed in a vacuum drying oven at temperatures between 70° C. and 100° C., e.g., at 50 mbar. The finished copolymer then forms the core with a ring of the perforated disk material around it. Also, a dye, e.g., Solvent Green 3, can be dissolved in the disk material for the haptic part. A small amount of HEMA can also be added. This brings it about that the haptic becomes less brittle. A haptic of low brittleness is also achieved by PEMA or an MMA-ethyl methacrylate copolymer.

The procedure described results in a tight bond between the core made of the HEMA-MMA- or HEMA-ethyl methacrylate and the ring of PMMA, PEMA or MMA-ethyl methacrylate copolymer surrounding this core. By the polymerization of the core within the ring or perforated disk, from which the haptic can be obtained for the intraocular lens, by mechanical working, for example, an outstanding bond is obtained between the hydratable core of HEMA-MMA- or HEMA-ethyl methacrylate copolymer which forms the optical lens part of the intraocular lens and the ring of PMMA, PEMA or MMA-ethyl methacrylate copolymer. The hydrated copolymer, which has a high hydrolysis stability, folds well for implantation. In the case of a blank of a uniform lens material, the polymerization is performed as in the case of the core material in a polymerization mold.

On account of the heavy crosslinking of the material of the haptic part, the finished intraocular lens can be treated by steam sterilization in the hydrated state. This has the desirable side effect of freedom from residues and degradation products and makes possible parametric release without outgassing after ethylene oxide (EO) sterilization or heat treatment after radiation sterilization.

The stable bond between the optical lens part and the haptic part results from the chemical kindred between the HEMA-MMA or HEMA-ethyl methacrylate copolymer and the PMMA, PEMA or MMA-ethyl methacrylate copolymer and the use of the common crosslinking agent EGDMA.

Embodiments of the compositions of the haptic ring and optical lens part are given below.

| | Wt.-% |
|---|---|
| Haptic part | |
| 1. MMA or ethyl methacrylate | 94.79 |
| EGDMA | 5.00 |
| AIBN | 0.20 |
| Solvent Green 3 | 0.01 |
| 2. MMA or ethyl methacrylate | 84.70 |
| EGDMA | 15.00 |
| AIBN | 0.05 |
| Solvent Green 3 | 0.25 |
| Optic part or lens material only | |
| 1. HEMA | 89.70 |
| MMA or ethyl methacrylate | 8.00 |
| EGDMA | 2.00 |
| MAO-2-HBP | 0.25 |

-continued

| | Wt.-% |
|---|---|
| AIBN | 0.05 |
| 2. HEMA | 82.00 |
| MMA or ethyl methacrylate | 16.00 |
| EGDMA | 0.50 |
| MAO-2-HBP | 1.00 |
| AIBN | 0.50 or less |

What is claimed is:

1. An intraocular lens, comprising:

a foldable optical lens part consisting of a hydroxyethyl methacrylate-methyl methacrylate copolymer; and a harder haptic part consisting of polymethyl methacrylate, wherein the copolymer of the optical lens part and the polymer of the haptic part are crosslinked to a three-dimensional matrix by a common cross-linking agent which is ethylene glycol dimethacrylate, and wherein the hydroxyethyl methacrylate in the copolymer of the optical lens part is at least 80 wt.-% and the methyl methacrylate is about 4 to 17 wt.-%.

2. An intraocular lens according to claim 1, wherein the percentage of hydroxyethyl methacrylate in the copolymer of the optical lens part is approximately up to 95 wt.-%.

3. An intraocular lens according to claim 1, further comprising an ultraviolet absorber having at least one functional reaction group that is polymerized into the matrix of the optical lens part.

4. An intraocular lens according to claim 3, wherein the functional reaction group is $=CH_2$.

5. An intraocular lens according to claim 3, wherein the ultraviolet absorber is 4-methacryloxy-2-hydroxybenzophenone.

6. A method of making an intraocular lens, said method comprising:

placing a solution consisting of hydroxyethyl methacrylate and methyl methacrylate into a polymethyl methacrylate ring;

polymerizing the solution, thereby forming a lens blank; and forming an intraocular lens part from said blank comprising a foldable optical lens part consisting of a hydroxyethyl methacrylate-methyl methacrylate copolymer, wherein the hydroxyethyl methacrylate is at least 80 wt.-% and the methyl methacrylate is about 4 to 17 wt.-%.

7. A method according to claim 6, further comprising pre-swelling the ring before said polymerizing.

8. A method according to claim 6, further comprising, before said polymerizing, diffusing methyl methacrylate out of the solution into the ring.

* * * * *